US008911979B2

(12) United States Patent
Foody et al.

(10) Patent No.: US 8,911,979 B2
(45) Date of Patent: Dec. 16, 2014

(54) RECOVERY OF INORGANIC SALT DURING PROCESSING OF LIGNOCELLULOSIC FEEDSTOCKS

(75) Inventors: Brian Foody, Ottawa (CA); Jeffrey S. Tolan, Ottawa (CA); Ziyad Rahme, Ottawa (CA); Vijay Anand, Ottawa (CA)

(73) Assignee: Iogen Energy Corporation, Ontario (CA)

( * ) Notice: Subject to any disclaimer, the term of this patent is extended or adjusted under 35 U.S.C. 154(b) by 161 days.

(21) Appl. No.: 13/569,308

(22) Filed: Aug. 8, 2012

(65) Prior Publication Data

US 2012/0329096 A1    Dec. 27, 2012

Related U.S. Application Data

(62) Division of application No. 12/539,645, filed on Aug. 12, 2009, now Pat. No. 8,247,203, which is a division of application No. 11/104,698, filed on Apr. 13, 2005, now Pat. No. 7,585,652.

(60) Provisional application No. 60/561,787, filed on Apr. 13, 2004.

(51) Int. Cl.
| | | |
|---|---|---|
| C12P 7/08 | (2006.01) |
| C12P 7/12 | (2006.01) |
| C13K 1/02 | (2006.01) |
| C13K 1/06 | (2006.01) |
| B01D 61/14 | (2006.01) |
| B01B 1/00 | (2006.01) |
| B01D 15/18 | (2006.01) |
| B01D 15/36 | (2006.01) |
| B01D 61/44 | (2006.01) |
| C05B 7/00 | (2006.01) |
| C05C 3/00 | (2006.01) |
| C05D 1/00 | (2006.01) |
| C05D 1/02 | (2006.01) |
| C05D 5/00 | (2006.01) |
| C05F 11/00 | (2006.01) |
| C12P 3/00 | (2006.01) |
| C12P 7/06 | (2006.01) |
| C12P 7/10 | (2006.01) |
| C12P 19/02 | (2006.01) |

(52) U.S. Cl.
CPC .............. *B01D 61/147* (2013.01); *B01B 1/005* (2013.01); *B01D 15/1821* (2013.01); *B01D 15/365* (2013.01); *B01D 61/44* (2013.01); *C05B 7/00* (2013.01); *C05C 3/00* (2013.01); *C05D 1/00* (2013.01); *C05D 1/02* (2013.01); *C05D 5/00* (2013.01); *C05F 11/00* (2013.01); *C12P 3/00* (2013.01); *C12P 7/06* (2013.01); *C12P 7/10* (2013.01); *C12P 19/02* (2013.01); *Y02E 50/16* (2013.01); *Y02E 50/17* (2013.01)
USPC ................ 435/163; 435/164; 127/37; 127/39

(58) Field of Classification Search
None
See application file for complete search history.

(56) References Cited

U.S. PATENT DOCUMENTS

| | | |
|---|---|---|
| 4,048,341 A | 9/1977 | Lagestrom et al. |
| 4,101,338 A | 7/1978 | Rapaport et al. |
| 4,237,226 A | 12/1980 | Grethlein |
| 4,321,360 A | 3/1982 | Blount |
| 4,356,196 A | 10/1982 | Hultquist |
| 4,461,648 A | 7/1984 | Foody |
| 4,556,430 A | 12/1985 | Converse et al. |
| 4,600,590 A | 7/1986 | Dale |
| 4,644,060 A | 2/1987 | Chou |
| 5,037,663 A | 8/1991 | Dale |
| 5,124,004 A | 6/1992 | Grethlein et al. |
| 5,171,592 A | 12/1992 | Holtzapple et al. |
| 5,177,008 A | 1/1993 | Kampen |
| 5,536,325 A | 7/1996 | Brink |
| 5,620,877 A | 4/1997 | Farone et al. |
| 5,782,982 A | 7/1998 | Farone et al. |
| 5,789,210 A | 8/1998 | Ho et al. |
| 5,865,898 A | 2/1999 | Holtzapple et al. |
| 5,932,456 A | 8/1999 | Van Draanen et al. |

(Continued)

FOREIGN PATENT DOCUMENTS

| | | |
|---|---|---|
| EP | 0884391 | 12/1998 |
| WO | WO 91/10740 | 7/1991 |

(Continued)

OTHER PUBLICATIONS

Lee, et al., "Recovery of ammonium sulfate from fermentation waste by electrodialysis", Water Research 37 (2003) 1091-99.

(Continued)

*Primary Examiner* — Thane Underdahl
(74) *Attorney, Agent, or Firm* — Fitzpatrick, Cella, Harper & Scinto

(57) ABSTRACT

A method for recovering inorganic salt during processing of a lignocellulosic feedstock is provided. The method comprises pretreating the lignocellulosic feedstock by adding an acid to the feedstock to produce a pretreated lignocellulosic feedstock. A soluble base is then added to the pretreated lignocellulosic feedstock to adjust the pH and produce a neutralized feedstock. The neutralized feedstock is then enzymatically hydrolyzed to produce an enzyme hydrolyzed feedstock and a sugar stream. Inorganic salt is recovered from either a stream obtained from the lignocellulosic feedstock prior to the step of pretreating, a stream obtained from the pretreated lignocellulosic feedstock, a stream obtained from the neutralized feedstock, a stream obtained from the sugar stream, or a combination of these streams. The inorganic salt may be concentrated, clarified, recovered and purified by crystallization, electrodialysis drying, or agglomeration and granulation, and then used as desired, for example as a fertilizer.

27 Claims, 1 Drawing Sheet

(56) References Cited

U.S. PATENT DOCUMENTS

| | | | |
|---|---|---|---|
| 6,043,392 | A | 3/2000 | Holtzapple et al. |
| 6,106,888 | A | 8/2000 | Dale et al. |
| 6,176,176 | B1 | 1/2001 | Dale et al. |
| 6,444,437 | B1 | 9/2002 | Sporleder et al. |
| 6,478,965 | B1 | 11/2002 | Holtzapple et al. |
| 6,589,760 | B1 | 7/2003 | Buchanan et al. |
| 6,608,184 | B2 | 8/2003 | Blount |
| 6,709,527 | B1 | 3/2004 | Fechter et al. |
| 6,939,544 | B2 | 9/2005 | Horwitz et al. |
| 2002/0164731 | A1 | 11/2002 | Eroma et al. |
| 2008/0102502 | A1 | 5/2008 | Foody et al. |

FOREIGN PATENT DOCUMENTS

| | | |
|---|---|---|
| WO | WO 02/18610 | 3/2002 |
| WO | WO 02/070753 | 9/2002 |
| WO | WO 03/046276 | 6/2003 |

OTHER PUBLICATIONS

Cao, et al., "Ethanol Production From Corn Cob Pretreated by the Ammonia Steeping Process Using Genetically Engineered Yeast", Biotechnology Letters vol. 18, No. 9 (Sep. 1996) 1013-18.

Thompson, et al., "Post-Harvest Processing Methods for Reduction of Silica and Alkali Metals in Wheat Straw", Applied Biochemistry and Biotechnology, vol. 105-108 (2003) 205-18.

Wooley, et al., "Lignocellutosic Biomass to Ethanol Process Design and Economics Utilizing Co-Current Dilute Acid Prehydrolysis and Enzymatic Hydrolysis Current and Futuristic Scenarios", National Renewable Energy Laboratory (NRELL) (Jul. 1999) 13-18.

Fontana, et al., "Cassava Starch Maltodextrinization/Monomerization through Thermopressurized Aqueous Phosphoric Acid Hydrolysis", Applied Biochemistry and Biotechnology vol. 91-93 (2001) 469-78.

Pessona, et al., "Acid Hydrolysis of Hemicellulose from Sugarcane Bagasse", Brazilian Journal of Chemical Engineering vol. 14, No. 3 (1997) 291-97.

Dien, et al., "Conversion of corn milling fibrous co-products into ethanol by recombinant *Escherichia coli* strains K011 and SL40", World Journal of Microbiology & Biotechnology vol. 13 No. 6, (1997) 619-25.

Lewis, Richard J., Sr., Hawley's Condensed Chemical Dictionary (14th Edition) (2002), John Wiley & Sons 5 pgs.

Kimbal, John W., Kimball's Biology Pages; Copyright 2006, Accessed May 1, 2006, Available online at :http://users.rcn.com/jkimball.ma.ultranet/BiologyPages/F/FramesVersion.html 6 pgs.

Ruthven, Douglas M. (Editor), Encycolopedia of Separation Technology; ISBN: 0471161241 (May 1997) 1776.

Bailar, John, Comprehensive Inorganic Chemisty; ISBN 008017275 (1973) 5 pgs.

Atkins, Peter Atkins, Duward Shriver, Inorganic Chemistry, Third Edition; ISBN: 0716736241 (Jan. 1999) 763.

ASL-Clemson, Agricultural Service Laboratory, Plant Tissue Analysis, Clemson Extension; Guidelines for Sampling and Interpreting Results, Accessed May 1, 2006, Available Online at www.clemson.edu/agsrvlb/plantsampling.htm 16 pgs.

Larrson, et al., "Recirculation of Process Water in the Production of Ethanol from Softwood", Bioresource Technology 60 (1997) 143-51.

Shambe, et al., "Acid and enzymic hydrolysis of chaotropically pretreated millet stalk, acha and rice straws and conversion of the products to ethanol", Enzyme and Microbial Technology vol. 7, No. 3 (1985) 115-20.

Wyman, Charles E., "Biomass Ethanol: Technical Progress, Opportunitites, and Commercial Challenges", Annu. Rev Energy Environ, vol. 24 (1999) 189-26.

Schell, et al., "Dilute-Sulfuric Acid Pretreatment of Corn Stover in Pilot Scale Reactor", Applied Biochemistry and Biotechnology vol. 105-108 (2003) 69-85.

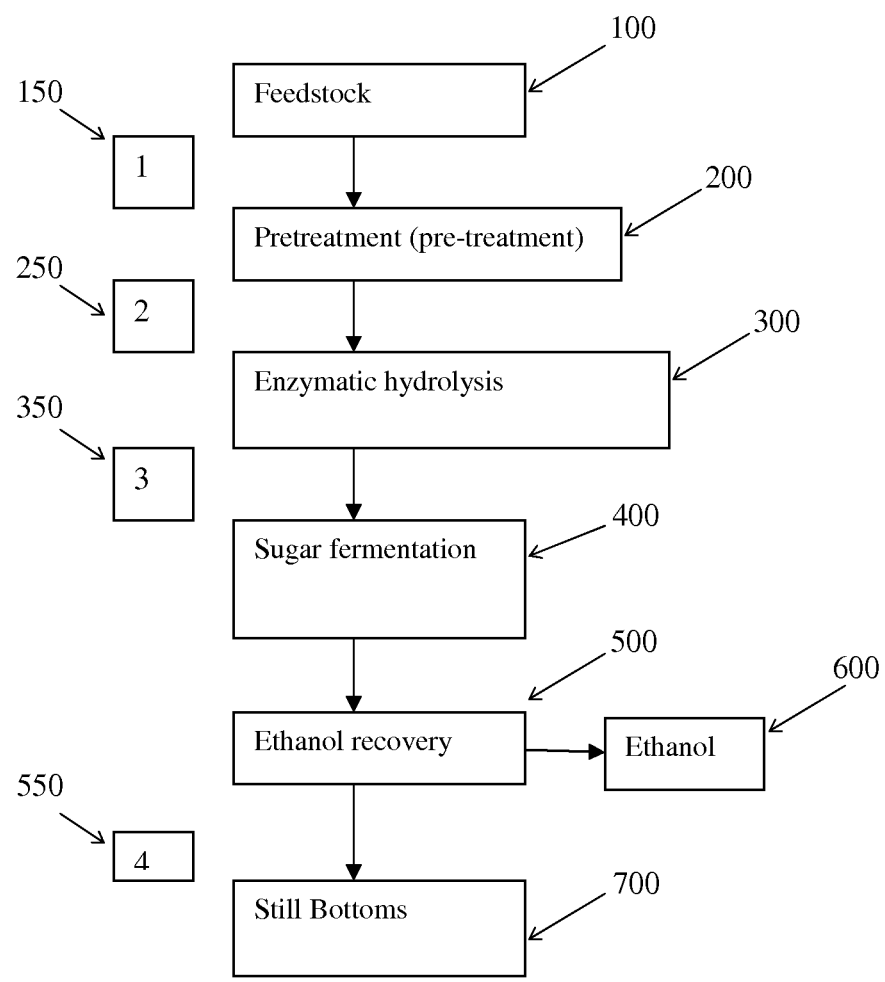

RECOVERY OF INORGANIC SALT DURING PROCESSING OF LIGNOCELLULOSIC FEEDSTOCKS

RELATED APPLICATION

This application is a division of application Ser. No. 12/539,645 filed Aug. 12, 2009, now U.S. Pat. No. 8,247,203 which in turn is a division of application Ser. No. 11/104,698, filed Apr. 13, 2005 (now U.S. Pat. No. 7,585,652), which in turn claims the priority benefit of a provisional application No. 60/561,787, filed Apr. 13, 2004, all of which are incorporated by reference herein.

FIELD OF INVENTION

The present invention relates to a method for processing lignocellulosic feedstocks. More specifically, the present invention provides a method for recovering inorganic salt during the processing of lignocellulosic feedstocks.

BACKGROUND OF THE INVENTION

Fuel ethanol is currently made from feedstocks such as corn starch, sugar cane, and sugar beets. The production of ethanol from these sources cannot grow much further, as most of the farmland suitable for the production of these crops is in use. In addition, these feedstocks can be costly since they compete with the human and animal food chain. Finally, the use of fossil fuels, with the associated release of carbon dioxide and other products, for the conversion process is a negative environmental impact of the use of these feedstocks.

The production of fuel ethanol from cellulosic feedstocks provides an attractive alternative to the fuel ethanol feedstocks used to date. Cellulose is the most abundant natural polymer, so there is an enormous untapped potential for its use as a source of ethanol. Cellulosic feedstocks are also inexpensive, as they do not have many other uses. Another advantage of producing ethanol from cellulosic feedstocks is that lignin, which is a byproduct of the cellulose conversion process, can be used as a fuel to power the conversion process, thereby avoiding the use of fossil fuels. Several studies have concluded that, when the entire cycle is taken into account, the use of ethanol produced from cellulose generates close to nil greenhouse gases.

The cellulosic feedstocks that are the most promising for ethanol production include (1) agricultural wastes such as corn stover, wheat straw, barley straw, canola straw, rice straw, and soybean stover; (2) grasses such as switch grass, miscanthus, cord grass, and reed canary grass, (3) forestry wastes such as aspen wood and sawdust, and (4) sugar processing residues such as bagasse and beet pulp.

Regardless of the feedstock used, the first step involves handling and size reduction of the material. The feedstock must be conveyed into the plant. This is contemplated to be carried out by trucks, followed by placing the feedstock on conveyor belts to be conveyed into the plant. The feedstock particles must then be reduced to the desired size to be suitable for handling in the subsequent processing steps.

The first process step is a chemical treatment, which usually involves the use of steam along with acid or alkali to break down the fibrous material. The chemical treatment is carried out for either of two primary processes—acid hydrolysis and enzymatic hydrolysis—used to convert the feedstock to sugar.

In the acid hydrolysis process, the feedstock is subjected to steam and sulfuric acid at a temperature, acid concentration, and length of time that are sufficient to hydrolyze the cellulose to glucose and hemicellulose to xylose and arabinose. The sulfuric acid can be concentrated (25-90% w/w) or dilute (3-8% w/w). The glucose, xylose and arabinose are then fermented to ethanol using yeast, and the ethanol is recovered and purified by distillation. A problem with concentrated acid hydrolysis is that the high levels of concentrated acid required necessitate the recovery and re-use of over 99% of the acid in the process. The recovery of this high proportion of acid is especially difficult due to the high viscosity and corrosivity of concentrated acid.

In the enzymatic hydrolysis process, the steam temperature, concentration of acid, and treatment time are chosen to be significantly milder than that in the acid hydrolysis process, such that the exposed cellulose surface area is greatly increased as the fibrous feedstock is converted to a muddy texture. Much of the hemicellulose is hydrolyzed, but there is little conversion of the cellulose to glucose. The cellulose is hydrolyzed to glucose in a subsequent step that uses cellulase enzymes, and the steam/acid treatment in this case is known as pretreatment. The acids used in pretreatment include sulfuric acid in steam explosion and batch and continuous flow pretreatments and also sulfurous acid and phosphoric acid.

The hydrolysis of the cellulose, whether by acid hydrolysis or by cellulase enzymes after pretreatment, is followed by the fermentation of the sugar to ethanol. The ethanol is then recovered by distillation.

There are several problems that must be overcome in order for the conversion of cellulosic biomass to sugar or ethanol to be commercially viable. In particular, there is a large amount of inorganic salt present in the feedstock and generated in the process. The inorganic salt has an adverse impact on the pretreatment, enzymatic hydrolysis, and yeast fermentation processes. In addition, the purchase of the acid and the alkali and the disposal of the salt is costly.

Neutral salts consist of cation(s), which provide a positive charge, and anion(s), which provide a negative charge. The most prevalent element in the feedstock that is a source of cations is potassium. Other elements in the feedstocks that are significant sources of cations include calcium, sodium, and magnesium, at concentrations of about $\frac{1}{3}$, $\frac{1}{7}$, and $\frac{1}{10}$ that of potassium. Most of the potassium, calcium, sodium, and magnesium in the feedstocks is complexed with organic compounds, such as proteins or carboxylic acids, or exists in the form of oxides or oxalates. The feedstocks are slightly alkaline with this "excess" of cations, as the concentration of anions is low.

The addition of, for example, sulfuric acid to the feedstock as part of the chemical treatment forms the mixtures of sulfuric acid and acidified sulfate salts, which include potassium bisulfate, calcium sulfate, sodium bisulfate, and magnesium bisulfate. Analogous acidified salts are formed with the use of other acids. These acidified salts are more water soluble than the complexed cations, and are released into solution upon acid addition. The presence of the cations thereby increases the amount of acid required in the chemical treatment. The high acid and acidic salt concentrations result in some degradation of sugar, including xylose, during the pretreatment.

The acid used in the pretreatment must be neutralized prior to the enzymatic hydrolysis of the cellulose or fermentation of the sugar. Cellulase enzymes produced by the fungus *Trichoderma*, which are the leading sources of cellulase for cellulose conversion, exhibit optimum activity at pH 4.5 to 5.0. These enzymes exhibit little activity below pH 3. Microbes that ferment the sugar include yeast and *Zymomonas* bacteria. The yeast are active at pH 4-5 while the *Zymomonas* are active at pH 5-6. An acidic chemical treatment is often carried out at a pH of about 0.8 to 2.0, so a significant amount of alkali must be added to increase the pH to the range that is required for microbial fermentation and enzymatic hydrolysis.

When an acidic pretreatment is carried out, the alkaline that is usually used for neutralization of the acid is sodium hydroxide, but potassium hydroxide and ammonium hydroxide have also been reported. The high levels of these compounds that are required increase the cost of the process.

Although the neutralized slurry is at a pH range that is compatible with yeast or fermenting bacteria or cellulase enzymes, the inorganic salt concentration is high enough to be inhibitory to the microbes or enzymes. The inorganic salt can also cause a degradation of the sugar, particularly the xylose, in evaporation and distillation processes that are carried out downstream of the hydrolysis.

Alkali that is used during processing of the lignocellulosic feedstock can be either soluble or insoluble. An example of an insoluble alkali is lime, which is used to precipitate inhibitors of cellulase enzymes arising from the pretreatment. This process is known as over-liming and involves adding lime to the pretreated feedstock until an alkaline pH of between 9 and 12 is achieved. The limed material is then adjusted to pH 5 prior to enzyme hydrolysis using phosphoric acid, carbon dioxide or other convenient acids. Since overliming precipitates some of the inhibitors of the cellulase enzymes, it results in an improved enzymatic hydrolysis of the cellulose with existing pretreatment technologies. However, there are numerous problems associated with overliming including (1) disposal of the lime; (2) calcium precipitation which leads to downstream scaling; (3) the expense of the lime; and (4) the fact that the treatment is not completely effective in removing inhibitors of enzymes and yeast.

Wooley et al. (In Lignocellulosic Biomass to Ethanol Process Design and Economics Utilizing Co-Current Dilute Acid Prehydrolysis and Enzyme Hydrolysis Current and Future Scenarios, (1999) Technical Report, National Renewable Energy Laboratory pp. 16-17) describe a process of treating lignocellulosic material utilizing over-liming following acid pretreatment. Milled wood chips are first pretreated with dilute sulfuric acid followed by enzyme hydrolysis and fermentation. Following pretreatment, the resulting liquid and solids are flash cooled to vapourize a large amount of water and inhibitors of the downstream fermentation reaction. After ion exchange to remove acetic acid, the material is over-limed by adding lime to raise the pH to 10. The liquid is then adjusted to pH 4.5 which results in the formation of gypsum crystals ($CaSO_4$). These crystals can be removed from the liquid by hydrocyclone and rotary drum filtration in series. Although the process describes the removal of gypsum after acid treatment, the investigators do not address the problems associated with removal of insoluble calcium salt.

U.S. Pat. No. 6,043,392 (Holtzapple et al.) employs a pretreatment step with lime prior to recovering volatile fatty acids produced during the fermentation of lignocellulosic biomass by anaerobic or thermophilic bacteria. After the treatment, lime is removed by draining the lime-containing water from the biomass, followed by fermentation with anaerobic bacteria. The anaerobic organisms then convert the biomass to organic acids such as acetic acid, proprionic and butyric acids. The organic acids produced by these fermentation processes can be concentrated and converted to ketones by pyrolysis in a thermal converter. Any soluble and insoluble minerals present after pyrolysis can be recovered and sold as a fertilizer. Alternatively, the organic acids are treated with a tertiary amine and carbon dioxide to produce an acid/amine complex that decomposes to form an acid and an amine with different volatilities. The acid can then be separated from the amine by distillation and precipitated minerals that accumulate in the bottoms of the distillation column can be recovered. Although Holtzapple et al. describe an effective method for the isolation of organic acids produced during fermentation using an alkaline pretreatment, they do not demonstrate the applicability of their process using an acidic pretreatment, nor did they demonstrate the effectiveness of their pretreatment in improving enzymatic hydrolysis.

U.S. Pat. No. 6,478,965 (Holtzapple et al.) discloses a method for isolating carboxylate salts formed as a product during the fermentation of lignocellulosic biomass by anaerobic bacteria. A fermentation broth, which contains dilute carboxylate salt in aqueous solution, is contacted with a low molecular weight secondary or tertiary amine which has a high affinity for water and a low affinity for the carboxylate salt. This allows the water to be selectively extracted while the carboxylate salt remains in the fermentation broth and becomes concentrated so that it can be easily recovered. The carboxylate salt may be further concentrated by evaporation, dried or converted to a more concentrated carboxylic acid solution. While Holtzapple et al. describe an effective method for the isolation of carboxylate fermentation products, they do not address the recovery of inorganic salts from the feedstock itself or inorganic salts arising from the acids and bases used during the processing of the lignocellulosic feedstocks. Furthermore, the process disclosed does not include a step of acidic pretreatment prior to enzymatic hydrolysis and fermentation.

U.S. Pat. No. 5,124,004 (Grethlein et al.) discloses a method for concentrating an ethanol solution by distillation. The method first involves partially concentrating the ethanol solution by distillation and withdrawing a vapour stream. Next, the condensation temperature of the vapour is raised above the evaporation temperature of a re-boiler liquid used in the process (a heat-sink liquid). The vapour stream is then used to heat the re-boiler liquid and partially enriched vapour is then removed and condensed. The condensed stream is introduced to an extractive distillation column and concentrated in the presence of an added salt to increase the volatility of the ethanol. The invention provides the benefit that the heat requirement of distillation is reduced since vapour required to heat the system does not need to be provided by an external source. However, there is no discussion of recovering and removing the salts added during the final distillation step.

U.S. Pat. No. 5,177,008 (Kampen) discloses the recovery of fermentation by-products, namely glycerol, betaine, L-pyroglutamic acid, succinic acid, lactic acid and potassium sulfate, produced during the manufacture of ethanol from sugar beets. The process involves fermenting the raw material, collecting the ethanol by distillation and then recovering the by-products in the remaining still bottoms. The by-products are isolated by first centrifuging the still bottoms and performing microfiltration to further clarify the solution. The resulting permeate is then concentrated to a solids concentration of 50-75%. The concentrated solution is first subjected to a crystallization step to recover potassium sulfate and then passed to a chromatographic separation step for the subsequent recovery of glycerol, betaine, succinic acid, L-pyroglutamic acid or lactic acid. The potassium sulfate is present in the raw material and its concentration is increased by cooling the solution and/or by the addition of sulfuric acid as part of the crystallization. The process of Kampen has several advantages such as energy and water savings and high solids concentrations. However, there is no discussion of a chemical pretreatment of lignocellulosic material with acid or an alkali neutralization step prior to enzymatic hydrolysis and fermentation and the associated problems with the presence of sodium and magnesium salts arising from such a pretreatment. Furthermore, since Kampen et al. used sugar beets, they were able to crystallize potassium sulfate directly from the still bottoms, and they do not address the recovery from still bottoms of salt mixtures with high levels of impurities that do not crystallize. Acid pretreatment of lignocellulosic feedstocks results in mixtures of inorganic salts in the still bottoms that cannot be directly crystallized.

U.S. Pat. Nos. 5,620,877 and 5,782,982 (Farone et al.) disclose a method for producing sugars from rice straw using concentrated acid hydrolysis which, as set out above, is not a preferred pretreatment method. The method results in the production of quantitative yields of potassium silicate. In this method, the rice straw is treated with concentrated sulfuric acid at a concentration of between 25% and 90%. The resulting mixture is then heated to a temperature to effect acid hydrolysis of the rice straw. Subsequently, the mixture is separated from the remaining solids by pressing. The pressed solids can then be treated with 5% to 10% sodium hydroxide to extract silicic acid. Following the treatment with sodium hydroxide, the solids are heated and then pressed and washed with water to extract a liquid. The extracted liquid is then treated with an acid, which results in the formation of a precipitate that can be separated by filtration. The filtered material is then treated with bleach to produce silica gel that can be further treated to produce sodium silicate, potassium silicate or other useful materials. The method also employs a neutralization step using lime to precipitate soluble inorganic salts present in a sugar stream produced during fermentation. Lime is an insoluble base that can build up on process equipment downstream of its point of addition and decrease the efficiency of the process.

WO 02/070753 (Griffin et al.) discloses a leaching process to remove alkali from lignocellulosic feedstocks thereby decreasing the acid requirement for chemical treatment. The process includes milling the feedstock, followed by preconditioning it with steam and then contacting the feedstock with water to leach out the salts, protein, and other impurities. The water containing these soluble compounds is then removed from the feedstock. This process decreases the acid requirements in the subsequent pretreatment process, which increases the yield of xylose after pretreatment. However, the costs and problems associated with the salt arising from the acid or alkali added for chemical treatment and the alkali or acid added after chemical treatment for adjustment of the pH are not addressed. Furthermore, disposing of the leachate is inconvenient and adds to the cost of the process.

U.S. Pat. No. 4,321,360 (Blount) discloses the preparation of ethanol from lignocellulosic feedstocks; however, there is no discussion of salt processing or recovery arising during this process. U.S. Pat. No. 6,608,184 (Blount) describes the production of ethanol, salt, and several other organic products from sewer sludge comprising sewered cellulose waste material (rather than a lignin-cellulose material). This process involves mixing sewer sludge with water and sodium hydroxide, or an acid (sulfuric or hydrochloric acid). The slurry containing acid or alkali is then heated to hydrolyze the cellulose in the sludge, and an excess of water is added to dissolve the organic compounds. The aqueous material is then separated from the insolubles and evaporated to concentrate the solution and crystallize out the carbohydrates. The carbohydrates are filtered off, slurried in water, and fermented to ethanol using yeast. The aqueous solution containing ammonium sulfate and other compounds may then be used as a fertilizer. Alternatively, the salt is separated from the sugar by membrane filtration and then the salt is evaporated and dried.

U.S. Pat. No. 6,709,527 (Fechter et al.) discloses a process of treating an impure cane-derived sugar juice to produce white sugar and white strap molasses. The process involves subjecting the sugar juice to microfiltration/ultrafiltration to decrease the levels of suspended solids, organic non-sugar impurities and/or colour. The sugar juice is next subjected to ion exchange with a strong acid cation exchange resin in the hydrogen form and then to ion exchange with an anion ion exchange resin in the hydroxide form. Potassium-based fertilizer components can be obtained by regenerating the strong acid cation exchange resin with a strong acid such as hydrochloric acid or nitric acid to produce an acid stream rich in potassium salt. Ammonium-based fertilizer components can be obtained by regenerating the anion ion exchange resin with a strong or weak base such as sodium or potassium hydroxide and ammonium hydroxide to obtain an alkaline stream which is rich in nitrogen. After ion exchange, the resulting sugar solution is concentrated to produce a syrup, which is crystallized twice to produce impure crystallized sugar and white strap molasses. Although the patent describes the production of potassium and ammonium-based fertilizer components, there is no discussion of the recovery of inorganic salts arising from an acidic pretreatment and neutralization step.

U.S. Pat. No. 4,101,338 (Rapaport et al) disclose the separation of sucrose from impurities in sugar cane molasses. Rapaport et al. teach the pretreatment of a molasses stream to remove a significant amount of organic non-carbohydrate impurities and colour. The pretreatment can be carried out by precipitation with iron salts, such as ferric chloride or ferric sulfate. The insoluble flocculants are then removed from the molasses stream and the soluble iron salts are removed by the addition of lime and phosphoric acid or phosphate salts. The pretreatment may also be carried out by other processes which include: centrifugation, with removal of the cake; precipitation by adding ethanol to the molasses stream; and filtering the molasses across a membrane of cellulose acetate. Regardless of the pretreatment process, the purpose is to decrease the amount of organic non-carbohydrate impurities so that a subsequent step of ion exclusion chromatography will separate the carbohydrate fraction from the dissolved impurities. Rapaport et al. report that the pretreatment decreased the ash content to 10% and the organic non-sugar content to 16.3% of the solids present.

Organic non-carbohydrate impurities, within a lignocellulosic system, cannot be removed by the methods of U.S. Pat. No. 4,101,338 (Rapaport et al.) According to Rapaport's method, the amount of solids precipitated by iron salts or ethanol is modest and no solids are removed by centrifugation. By contrast, the sugar streams produced during the processing of lignocellulosic feedstock have a much higher level of organic non-carbohydrate impurities and inorganic salts. Rapaport et al. do not address the processing of such concentrated streams. Furthermore, the use of cellulose acetate membranes in a lignocellulosic system would not be feasible since such membranes would be destroyed by cellulase enzymes.

A process for the pretreatment, enzymatic hydrolysis and sugar fermentation of lignocellulosic feedstocks is required that addresses the problems associated with high inorganic salt concentrations in the feedstock and in the process. The development of such a process would represent a significant step forward in the commercialization of ethanol production from lignocellulosic biomass.

SUMMARY OF THE INVENTION

The present invention relates to a method for processing lignocellulosic feedstocks. More specifically, the present invention provides a method for recovering inorganic salt during the processing of lignocellulosic feedstocks.

It is an object of the invention to provide an improved method for recovery of inorganic salt during processing of lignocellulosic feedstocks.

According to the present invention, there is provided a method (A) for recovering inorganic salt during processing of a lignocellulosic feedstock comprising:

a. pretreating the lignocellulosic feedstock by adding one or more than one acid to the lignocellulosic feedstock to produce a pretreated lignocellulosic feedstock;

b. adding one or more than one soluble base to the pretreated lignocellulosic feedstock to adjust the pretreated lignocellulosic feedstock to a pH of about 4.0 to about 6.0 to produce a neutralized feedstock;

c. enzymatically hydrolyzing the neutralized feedstock to produce a sugar stream and an enzyme hydrolyzed feedstock; and d. recovering the inorganic salt from a stream produced from the lignocellulosic feedstock prior to the step of pretreating (step a.), a stream obtained from the pretreated lignocellulosic feedstock, a stream obtained from the neutralized feedstock, the sugar stream, or a combination thereof.

The lignocellulosic feedstock used in the method as described above may be selected from the group consisting of corn stover, wheat straw, barley straw, canola straw, rice straw, oat straw, soybean stover, grass, switch grass, miscanthus, cord grass, and reed canary grass, aspen wood, sawdust, bagasse and beet pulp. Preferably, the lignocellulosic feedstock contains from about 0.2% to about 4% (w/w) potassium.

The present invention also pertains to the method (A) described above, wherein, in the step of recovering (step d.), the inorganic salt is recovered by ion exclusion. The step of recovering may be followed by crystallization of the inorganic salt. The inorganic salt may comprise ammonium sulfate salts, ammonium phosphate salts, potassium sulfate salts, ammonium sulfite salts, potassium sulfite salts, sodium sulfate salts, sodium sulfite salts, magnesium sulfate, ammonium chloride, potassium chloride, magnesium chloride or a mixture thereof. Preferably, the inorganic salt is soluble. The ammonium sulfite salts, sodium sulfite salts, potassium sulfite salts, or a mixture thereof may be converted to sulfate salts by oxidation before or after the step of recovering (step d.).

The present invention provides a method (A) as described above, wherein the inorganic salt may be concentrated by evaporation, membrane filtration, or a combination thereof prior to recovery to produce a concentrated solution comprising the inorganic salt. The concentrated solution may be clarified by membrane filtration, plate and frame filtration, or centrifugation prior to recovery.

The present invention also provides a method (A) described above, wherein the step of pretreatment (step a.) comprises a method selected from the group consisting of batch dilute acid hydrolysis, continuous dilute acid hydrolysis, steam explosion and extrusion.

The one or more than one acid may be selected from the group consisting of sulfuric acid, sulfurous acid, sulfur dioxide, phosphoric acid, and a combination thereof. The one or more than one soluble base may be selected from the group consisting of ammonia, ammonium hydroxide, potassium hydroxide and sodium hydroxide.

Furthermore, the present invention pertains to the method (A) as described above, wherein the step of pretreating (step a.) is performed at a temperature from about 160° C. to about 280° C., at a pH from about 0.4 to about 2.0 and/or for a period of time from about 0.1 to about 30 minutes.

Furthermore, the present invention pertains to the method (A) described above further comprising the steps of:

e. fermenting the sugar stream to produce a fermentation broth comprising ethanol; and f. distilling the fermentation broth to produce concentrated ethanol and still bottoms.

Optionally, the inorganic salt may be recovered from the still bottoms followed by purifying the inorganic salt. Prior to the step of recovering the inorganic salt from the still bottoms, the concentration of the still bottoms may be increased by evaporation, membrane filtration, or a combination thereof, to produce concentrated still bottoms, followed by a step of ion exclusion chromatography using a simulated moving bed (SMB) process. The concentrated still bottoms may be clarified by microfiltration, plate and frame filtration or centrifugation prior to the step of ion exclusion chromatography. The step of purifying the inorganic salt may comprise crystallization of the inorganic salt or electrodialysis, drying or agglomeration and granulation.

The present invention provides the method (A) as described above, wherein prior to the step of pretreating (step a.), the lignocellulosic feedstock is pressed, leached, or a combination thereof to produce a leachate and wherein the leachate is combined with one or more than one soluble inorganic salt stream obtained from the pretreated feedstock, the neutralized feedstock, the sugar stream, or a combination thereof to produce a combined salt stream.

Furthermore, the inorganic salt present in the combined salt stream may be concentrated by evaporation, membrane filtration, or a combination thereof to produce a concentrated salt solution. The concentrated salt solution may be clarified to produce a clarified salt solution. The inorganic salt may be recovered from the clarified salt solution by ion exclusion chromatography.

Furthermore, there is provided the method (A) as described, wherein after the step of enzymatically hydrolyzing (step c.), the sugar stream is separated from the enzyme hydrolyzed feedstock to form a solid residue and a sugar hydrolyzate stream. The inorganic salt may be concentrated by evaporation, membrane filtration, or a combination thereof.

The present invention also provides a method (A) as described, wherein, in the step of pretreating (step a.), at least a portion of hemicellulose in the feedstock is hydrolyzed to produce one or more than one sugar monomer selected from the group consisting of xylose, arabinose, mannose, galactose and a combination thereof. Furthermore, in the step of enzymatically hydrolyzing (step c.), one or more than one cellulase enzyme may be added to the neutralized feedstock so that at least a portion of cellulose in the neutralized feedstock is hydrolyzed to produce glucose.

The present invention also pertains to a method (B) for recovering inorganic salt during processing of a lignocellulosic feedstock comprising:

a. pretreating the lignocellulosic feedstock by adding one or more than one acid to the lignocellulosic feedstock to produce a pretreated lignocellulosic feedstock;

b. adding one or more than one soluble base to the pretreated lignocellulosic feedstock to adjust the pretreated lignocellulosic feedstock to a pH of about 4.0 to about 6.0 to produce a neutralized feedstock;

c. enzymatically hydrolyzing the neutralized feedstock to produce a sugar stream and an enzyme hydrolyzed feedstock;

d. fermenting the sugar stream to produce a fermentation broth comprising ethanol;

e. distilling the fermentation broth to produce concentrated ethanol and still bottoms; and f. recovering the inorganic salt from the still bottoms to produce a recovered inorganic salt.

There is provided the method (B) described above further comprising the steps of purifying the recovered inorganic salt to obtain a purified inorganic salt and producing a product comprising the purified inorganic salt. The step of purifying may comprise performing ion exclusion chromatography, followed by electrodialysis, drying, agglomeration and granulation, or crystallization.

The present invention provides a process for the conversion of a lignocellulosic feedstock to sugar, and optionally fermenting the sugar to ethanol. The process further involves the recovery of inorganic salts formed during the conversion process and, optionally, the recovery of salts from the initial feedstock. The recovery of the inorganic salt may be carried out by ion exclusion followed by electrodialysis, drying, agglomeration and granulation, or crystallization. The recovered inorganic salts, which can include potassium sulfate salts, ammonium sulfate salts, ammonium phosphate salts, sodium phosphate salts, sodium sulfate, other salts, and mixtures of these salts, may be used for any desired purpose, for example as a fertilizer.

The process of the present invention overcomes several disadvantages of the prior art by taking into account the difficulties in the conversion of lignocellulosic feedstocks to sugar and then ethanol. By removing inorganic salt during the processing of lignocellulosic feedstock, several of the steps operate more efficiently, for example enzymatic hydrolysis, or fermentation of sugar to ethanol, as the inhibitory effect of the salt is reduced. Furthermore, the inorganic salts recovered during this process and the value generated from these salts help offset the cost associated with the use of these salts. The invention also allows for removing inorganic salts from the feedstock, which decreases the acid requirement and assists in overcoming any adverse effect the feedstock salts can have on the conversion process. The present invention offers significant advances in the production of sugar, ethanol, and other products from lignocellulosic feedstocks.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows a schematic outline of the process of the present invention, and indicates several stages where inorganic salt may be removed and recovered (indicated as stages 1-4).

DETAILED DESCRIPTION

The present invention relates to a method for processing lignocellulosic feedstocks. More specifically, the present invention provides a method for recovering inorganic salt during the processing of lignocellulosic feedstocks.

The following description is of a preferred embodiment.

The present invention provides a process for the recovery of inorganic salt during the conversion of a lignocellulosic feedstock to sugar. The inorganic salt may be used as fertilizer or for other purposes as desired.

Therefore, the present invention provides a method (A) for recovering inorganic salt during processing of a lignocellulosic feedstock comprising:

a. pretreating the lignocellulosic feedstock by adding one or more than one acid to the lignocellulosic feedstock to produce a pretreated lignocellulosic feedstock;

b. adding one or more than one soluble base to the pretreated lignocellulosic feedstock to adjust the pretreated lignocellulosic feedstock to a pH of about 4.0 to about 6.0 to produce a neutralized feedstock;

c. enzymatically hydrolyzing the neutralized feedstock to produce a sugar stream and an enzyme hydrolyzed feedstock; and d. recovering the inorganic salt from a stream produced from the lignocellulosic feedstock prior to the step of pretreating (step a.), a stream obtained from the pretreated lignocellulosic feedstock, a stream obtained from the neutralized feedstock, the sugar stream obtained from the enzyme hydrolyzed feedstock, or a combination thereof.

Additionally, the above method may comprise steps including:

e. fermenting the sugar stream to produce a fermentation broth comprising ethanol; and f. distilling the fermentation broth to produce concentrated ethanol and still bottoms.

If desired, a salt stream may be recovered from the still bottoms (step f) and combined with any inorganic salt obtained in step d, above.

The present invention also provides a method (B) for recovering inorganic salt during processing of a lignocellulosic feedstock comprising:

a. pretreating the lignocellulosic feedstock by adding one or more than one acid, to the lignocellulosic feedstock to produce a pretreated lignocellulosic feedstock;

b. adding one or more than one soluble base to the pretreated lignocellulosic feedstock to adjust the pretreated lignocellulosic feedstock to a pH of about 4.0 to about 6.0 to produce a neutralized feedstock;

c. enzymatically hydrolyzing the neutralized feedstock to produce a sugar stream and an enzyme hydrolyzed feedstock;

d. fermenting the sugar stream to produce a fermentation broth comprising ethanol;

e. distilling the fermentation broth to produce concentrated ethanol and still bottoms; and f. recovering the inorganic salt from the still bottoms to produce a recovered inorganic salt.

The feedstock for the process is a lignocellulosic material. By the term "lignocellulosic feedstock", it is meant any type of plant biomass such as but not limited to non-woody plant biomass, cultivated crops such as, but not limited to grasses, for example but not limited to C4 grasses, such as switch grass, cord grass, rye grass, miscanthus, reed canary grass, or a combination thereof, or sugar processing residues such as baggase, or beet pulp, agricultural residues, for example, soybean stover, corn stover, rice straw, rice hulls, barley straw, corn cobs, wheat straw, canola straw, rice straw, oat straw, oat hulls, corn fiber, recycled wood pulp fiber, sawdust, hardwood, for example aspen wood and sawdust, softwood, or a combination thereof. Further, the lignocellulosic feedstock may comprise cellulosic waste material such as, but not limited to newsprint, cardboard, sawdust and the like. Lignocellulosic feedstock may comprise one species of fiber or alternatively, lignocellulosic feedstock may comprise a mixture of fibers that originate from different lignocellulosic feedstocks. Furthermore, the lignocellulosic feedstock may comprise fresh lignocellulosic feedstock, partially dried lignocellulosic feedstock, fully dried lignocellulosic feedstock or a combination thereof.

Lignocellulosic feedstocks comprise cellulose in an amount greater than about 20%, more preferably greater than about 30%, still more preferably greater than about 40% (w/w). The lignocellulosic feedstock also comprises lignin in an amount greater than about 10%, more preferably in an amount greater than about 15% (w/w). The lignocellulosic feedstock also comprises a combined amount of sucrose, fructose and starch in an amount less than about 20%, preferably less than about 10% (w/w). The weight percentages disclosed above are relative to the mass of the lignocellulosic feedstock as it exists prior to the step of adding (step b., above).

By the term "inorganic salt", it is meant salts that do not contain either a cation or an anion with carbon-hydrogen bonds. This term is meant to exclude salts containing acetate anions, oxalate anions and other organic anions. These salts, and other salts containing an anion with a carbon-hydrogen bond, are "organic salts".

Preferably, the inorganic salt is soluble. By the term "soluble inorganic salt", it is meant that the inorganic salt has a solubility in water that is at least 0.1 M at 20° C. Calcium hydroxide, lime and calcium sulfate are examples of insoluble inorganic salts.

Most lignocellulosic feedstocks contain 0.2% to 4% (w/w) potassium. Examples, which are not to be considered limiting in any manner, of the amount of potassium in several varieties of corn stover, barley straw, and wheat straw are shown in Table 1.

TABLE 1

2002 Lignocellulosic feedstock harvest potassium (% w/w) content

| Feedstock | Variety | Location | Potassium (%) |
| --- | --- | --- | --- |
| Corn Stover | Pioneer 33B51 | Nebraska | 0.73 |
| Corn Stover | Pioneer 33P67 | Nebraska | 2.07 |
| Corn Stover | Dekalb S3-32 | Iowa | 0.56 |
| Corn Stover | Dekalb 44-46 | Iowa | 0.44 |
| Corn Stover | Pioneer 33P67 | Iowa | 2.02 |
| Corn Stover | Pioneer 36R11 | Iowa | 0.61 |
| Corn Stover | Pioneer 36R11 | Minnesota | 1.01 |
| Corn Stover | NK 67T4 | Iowa | 1.72 |
| Barley Straw | AC Lacombe | Alberta | 1.94 |
| Barley Straw | AC Lacombe | Alberta | 1.57 |
| Barley Straw | AC Metcalfe | Alberta | 2.22 |
| Barley Straw | AC Metcalfe | Manitoba | 1.24 |
| Wheat Straw | Prodigy | Alberta | 1.37 |
| Wheat Straw | Prodigy | Alberta | 0.52 |
| Wheat Straw | Splendor | Alberta | 0.55 |
| Wheat Straw | Splendor | Alberta | 1.59 |
| Wheat Straw | CDC Stratus | Manitoba | 0.82 |
| Wheat Straw | AC Barrie | Manitoba | 0.38 |
| Wheat Straw | CDC Stratus | Manitoba | 0.61 |
| Wheat Straw | AC Metcalf | Manitoba | 0.97 |
| Wheat Straw | AC Barrie HRS Wheat | Manitoba | 0.44 |
| Wheat Straw | Durum | Manitoba | 0.86 |
| Wheat Straw | HRS Wheat | Manitoba | 0.67 |
| Wheat Straw | Caphorn | England | 0.62 |
| Wheat Straw | Gladiator | England | 0.95 |
| Wheat Straw | Histories | England | 0.67 |
| Wheat Straw | Histories | England | 0.79 |
| Wheat Straw | Consort | England | 0.68 |
| Wheat Straw | Consort | England | 1.12 |
| Wheat Straw | Consort | England | 1.14 |
| Wheat Straw | Caphorn | France | 1.62 |
| Wheat Straw | Excellenz | France | 1.34 |
| Wheat Straw | Gladiator | France | 1.73 |
| Wheat Straw | Caphorn | France | 1.16 |
| Wheat Straw | Gladiator | France | 1.12 |

In addition to potassium, other common cationic elements in lignocellulosic feedstocks include magnesium, sodium and calcium. The most prevalent inorganic anions are typically phosphate and chloride. The most prevalent inorganic salts may therefore include chloride and phosphate salts of potassium, magnesium, sodium and calcium. Organic salts such as oxalates and acetates are also present in many lignocellulosic feedstocks.

The lignocellulosic feedstock for the process described herein preferably contains potassium. The higher the inorganic salt or potassium concentration, the more beneficial the outcome of the process of the present invention. The presence of inorganic salts within the treated lignocellulosic feedstock leads to the degradation of xylose that is produced as a result of processing the lignocellulosic feedstock. Degradation of xylose results in reduced yields of sugar, ethanol or a combination thereof. Furthermore, any inorganic salt, for example potassium sulfate, that is recovered as a by-product during the processing of lignocellulosic feedstocks, may be used for a variety of purposes, for example within a fertilizer.

As a result of processing the lignocellulosic feedstock as described herein, product streams are produced that contain sugar, inorganic salts, organic salts and other by-products. The inorganic salt may be recovered from the product streams by ion exclusion or any other suitable method as would be known to one of skill in the art.

By the term "ion-exchange", it is meant a separation technique that employs a chemical reaction in which an ion from solution is exchanged for a similarly charged ion attached to an immobile solid particle. The ion exchange resins may be cation exchangers that have positively charged mobile ions available for exchange, or anion exchangers, whose exchangeable ions are negatively charged. The solid ion exchange particles may be either naturally occurring inorganic zeolites or synthetically produced organic resins.

By the term "ion exclusion", it is meant a separation technique that separates ionic species in solution from non-ionic species, or weakly ionic species from strongly ionic species, by employing a resin having a structure that allows the non-ionic species or weakly ionic species to diffuse into it while preventing more ionic species from entering the resin. The species with less ionic character then elutes after the more ionic species.

As used herein, the term "membrane filtration" refers to any process of filtering a solution with a membrane that is suitable for concentrating a solution. Included in this definition are microfiltration, which employs membranes of a pore size of 0.05-1 microns for the removal of particulate matter; ultrafiltration, which employs membranes with a cut-off of 500-50,000 mw for removing large soluble molecules; and reverse osmosis using nanofiltration membranes to separate small molecules from water. The term "reverse osmosis" refers to the separation of solutions having different solute concentrations with a semi-permeable membrane by applying sufficient pressure to the more concentrated liquid to reverse the direction of osmosis across the membrane. The term "nanofiltration" refers to processes that separate solutions of differing solute concentrations using reverse osmosis, but that employ membranes which are finer than those used in reverse osmosis.

In addition to concentrating a solution, microfiltration may be used for clarification.

Separation by ion exclusion may employ Simulated Moving Bed (SMB) technology. As used herein, the term "Simulated Moving Bed" or "SMB" refers to an ion exclusion chromatographic separation process that utilizes a set of columns interconnected in series in which liquid circulates in the unit by simultaneous shifting of the columns in the opposite direction. As used herein, this term encompasses Improved Simulated Moving Bed (ISMB) systems. A non-limiting example of an ISMB system is provided in Example 1. SMB is a preferred separation method for ion exclusion chromatography since solvent use is minimized, thereby leading to a greatly reduced cost of operation when compared to traditional batch chromatography methods.

Prior to separation by ion exclusion, the inorganic salt solution may be concentrated and clarified. Concentration may be carried out by evaporation or by microfiltration (0.14 microns) to remove particles, ultrafiltration (500-2000 mw cut off) to remove soluble lignin and other large molecules and reverse osmosis to increase solids to a concentration of about 12 to about 20%, or any amount therebetween, followed by evaporation. Following concentration, the solution may be clarified by microfiltration, plate and frame filtration or centrifugation.

After separation from the product stream, the inorganic salt may be crystallized, dried or subjected to electrodialysis or agglomeration and granulation, and used as desired, for example as a solid fertilizer. Alternatively, the inorganic salt may be concentrated as a wet slurry and used in a liquid form, for example as a liquid fertilizer. The remaining components within the product streams, for example sugar, may be further processed or collected, as desired.

By the term "electrodialysis", it is meant a separation process in which ions are transported across a semi-permeable membrane under the influence of an electric potential. The membrane may be either cation or anion selective to allow for the separation of cations or anions, respectively.

By the term "crystallization", it is meant any process for the formation of solid particles or crystals of a solute from a saturated solution. This can be carried out by concentration, cooling (under vacuum or with a heat exchanger), reaction displacement or equilibrium displacement.

By the term "agglomeration and granulation", it is meant process steps to modify particle size, for example, to improve bulk properties. Non-limiting examples of bulk properties that can be improved include, but are not limited to, dissolving behavior, form and stability of the granulated product and storage stability.

By the term "drying", it is meant any process for removing water, volatile components or other liquids from a solid material, to reduce the content of residual liquid to an acceptable low value. This includes, but is not limited to, direct and indirect drying. Direct drying refers to using direct contact of hot gases to drive off some, or all of the water, and indirect drying refers to contact with a heated surface as opposed to hot gas.

The inorganic salts in the product stream result from the lignocellulosic feedstock itself, and from the acids and bases used during the processing of the lignocellulosic feedstock. For example, the inorganic salt mixtures that arise from sulfuric acid include mixtures of sulfuric acid, sodium bisulfate, and disodium sulfate, depending on the pH of the system and on the total ionic concentration. For this discussion, these salt mixtures will be referred to as "sodium sulfate salts". Other salt mixtures may also be present in the product streams for example, but not limited to, ammonium sulfate salts (sulfuric acid, ammonium bisulfate, and diammonium sulfate); sodium sulfite salts, (sulfurous acid, sodium bisulfite, and disodium sulfite); ammonium sulfite salts (sulfuric acid, ammonium bisulfite, and diammonium sulfite), sodium phosphate salts (phosphoric acid, sodium dihydrogen phosphate, and disodium hydrogen phosphate), ammonium phosphate salts (phosphoric acid, diammonium hydrogen phosphate, and ammonium dihydrogen phosphate), potassium sulfate salts (sulfuric acid, potassium bisulfate, and dipotassium sulfate), potassium sulfite salts (sulfuric acid, potassium bisulfite, and dipotassium sulfite), and potassium phosphate salts (phosphoric acid, potassium dihydrogen phosphate, and dipotassium hydrogen phosphate).

The inorganic salts recovered from the process as described herein have value as a fertilizer; however, additional uses of the recovered salts may be exploited as desired. In the case of fertilizer, ammonium, potassium, sulfate, and phosphate salts are typically of value. Other compounds present, including inorganic salts of sodium and sulfite salts, may be of less value in fertilizer. However, these inorganic salts can be converted to forms of higher value. For example, which is not to be considered limiting, sodium salts can be converted to potassium salts by the use of ion exchange. In this example, sodium hydroxide may be used for some or all of the neutralization of sulfuric acid during the processing of a lignocellulosic feedstock and the sodium ion exchanged with potassium using a cation exchange resin. The resulting potassium salt may then be of more value as a fertilizer.

Additionally, sulfite salts can be converted to sulfate salts by oxidation with air or with oxidizing agents. For example, sulfurous acid or sulfur dioxide present in pretreatment may be used to oxidize the sulfite salts to sulfate for use in fertilizer.

The step of pretreatment increases the susceptibility of the lignocellulosic feedstock to hydrolysis by cellulase enzymes. The pretreatment is carried out to hydrolyze the hemicellulose, or a portion thereof, that is present in the lignocellulosic feedstock to monomeric sugars, for example xylose, arabinose, mannose, galactose, or a combination thereof. Preferably, the pretreatment is designed to carry out almost complete hydrolysis of the hemicellulose and a small amount of conversion of cellulose to glucose. The cellulose is hydrolyzed to glucose in a subsequent step that uses cellulase enzymes. During the pretreatment, typically a dilute acid, from about 0.02% (w/v) to about 1% (w/v), or any amount therebetween, is used for the treatment of the lignocellulosic feedstock. The preferred acid for pretreatment is sulfuric acid. Acid pretreatment is familiar to those skilled in the art, see for example U.S. Pat. No. 5,536,325 (Brink); U.S. Pat. No. 4,237,226 (Grethlein; which are incorporated herein by reference). Other methods that are known within the art may be used as required for preparation of a pretreated feedstock, for example, but not limited to, those disclosed in U.S. Pat. No. 4,556,430 (Converse; which are incorporated herein by reference).

Preferably, the step of reacting the acidified feedstock is performed at a temperature between about 100° C. to about 280° C., or any amount therebetween, for example a temperature of 100, 120, 140, 160, 180, 200, 220, 240, 260, 280° C., or any amount therebetween, at a pH from about pH 0.4 to about pH 2.5 or any amount therebetween, for example, a pH of 0.4, 0.6, 0.8, 1.0, 1.2, 1.4, 1.6, 1.8, 2.0, 2.2, 2.4, 2.5, or any amount therebetween, for about 5 seconds to about 60 minutes, or any amount therebetween, for example, for 5, 10, 20, 30, 40, 50, 60 seconds, or for 1.5, 2, 4, 6, 8, 10, 15, 20, 25, 30, 35, 40, 45, 50, 55, 60 minutes, and any amount therebetween. It is understood by those skilled in the art that the feedstock temperature is that of the feedstock itself, which might differ from the temperature measured outside the reaction chamber. Devices used to carry out this pretreatment include, but are not limited to sealed batch reactors, continuous extruders and steam guns.

A preferred pretreatment, without intending to be limiting, is steam explosion described in U.S. Pat. No. 4,461,648 Foody; which is incorporated herein by reference). A typical set of pretreatment conditions for processing lignocellulosic feedstocks is a temperature of about 170° C. to about 260° C., for a period of about 0.1 to about 30 minutes and/or at a pH of about 0.4 to about 2.0.

It is also within the scope of the present invention that a two-stage pretreatment process may be used, whereby the first stage improves the cellulose hydrolysis somewhat while solubilizing primarily the hemicellulose but little cellulose. The second stage then completes a full pretreatment. Using this method, the first stage reaction is run at a temperature of less than about 180° C. while the second stage reaction is run at a temperature of greater than about 180° C. Preferably, the first stage of the reaction is carried out at a temperature of about 60° C. to about 140° C., or an amount therebetween, for 0.25 to 24 hours, or any amount therebetween, and at a pH from about pH 0.5 to about pH 2.5, or any amount therebetween. More preferably, the first stage of pretreatment is carried out at a temperature of 100° C. to 130° C. for 0.5 to 3 hours at pH 0.5 to 2.5. While the second stage of reaction may be carried out at a temperature of 180° C. to 270° C., at pH 0.5 to 2.5 for a period of 5 seconds to 120 seconds. The two-stage pretreatment provides separate recovery of the soluble monomers from hemicellulose for downstream processing.

Furthermore, the lignocellulosic feedstock may be processed using the methods disclosed in WO 02/070753 (Griffin et al., which is incorporated herein by reference). A pretreatment process using flow-through hydrolysis is disclosed in U.S. Pat. No. 4,237,226 (Grethlein et al., which is incorporated herein by reference).

The low pH for acidic chemical treatments requires the addition of acid to the lignocellulosic feedstock. Any acid can be used to adjust the pH of the lignocellulosic feedstock. However, preferred acids are sulfuric acid, sulfurous acid, sulfur dioxide, and phosphoric acid, due to their low cost, effectiveness in pretreatment, and, in the case of sulfate and phosphate salts, their further use within a fertilizer. A suitable alternative to sulfuric acid is phosphoric acid.

The pretreated lignocellulosic feedstock may be processed to remove any inorganic salt present prior to addition of the soluble base to the lignocellulosic feedstock. For example, the pretreated feedstock may be washed to remove the sugar-acid mixture from the solids portion. The separated acid stream may then be neutralized and processed as described below for sugar fermentation or added into a sugar stream from the enzyme hydrolysis for fermentation. Alternatively, the pretreated feedstock may be washed to remove the sugar-acid mixture from the solids portion, and the wash stream treated with base prior to separating the inorganic salt from the sugar in the salt stream. After salt removal, the neutralized wash stream may be processed for sugar fermentation or enzymatic hydrolysis, as described below. The inorganic salt recovered from the wash stream obtained from the pretreated lignocellulosic feedstock may be concentrated, or dried as described herein.

The pretreated lignocellulosic feedstock is highly acidic. It is neutralized prior to enzymatic hydrolysis and sugar fermentation. Cellulase enzymes are active over a range of pH of about 3 to about 7, or any range therebetween, preferably, the pH is from about 4.0 to about 6.0, or any range therebetween, and more preferably the pH is from about 4.5 to about 5.0, or any range therebetween. For example, the pH is 3.0, 3.5, 3.7, 4.0, 4.2, 4.5, 4.7, 5.0, 5.2, 5.5, 6.0, 6.5, 7.0, or any amount therebetween. Yeast and Zymomonas bacteria are typically used for sugar fermentation. The optimum pH for yeast is from about pH 4 to about pH 5, while the optimum pH for Zymomonas is from about pH 5 to about pH 6. In principle, any soluble base can be used to adjust the pH of acidic material. However, it is preferred that the base used for pH adjustment of acid material is ammonia gas or ammonia dissolved in water for example, ammonium hydroxide. Sodium hydroxide or potassium hydroxide may also be used. These compounds are inexpensive, effective, and, in the case of ammonium and potassium salts, of high value if the inorganic salt is to be used in fertilizer.

By the term "soluble base", it is meant a base that has a solubility in water that is at least 0.1 M at 20° C. This term is meant to exclude salts that are slightly soluble or insoluble. Examples of bases that are excluded are $CaCO_3$ and $Ca(OH)_2$. Insoluble bases cannot be recovered according to the methods of the present invention. The term "base" is meant to encompass any species that, when dissolved in water, gives a solution with a pH that is more than 7.

Following the addition of the soluble base, enzymatic hydrolysis is carried out. Typically, the enzymes used for hydrolysis are cellulase enzymes that hydrolyze the cellulose to glucose. Any cellulase may be used, however, preferred cellulase enzymes are those made by the fungus *Trichoderma*. Preferably, the enzyme treatment is carried out between about 40° C. to about 60° C., or any temperature range therebetween, or between about 45° C. and about 55° C., or any temperature range therebetween. For example the enzyme treatment may be carried out at 40, 42, 44, 46, 48, 50, 52, 54, 56, 58, 60° C., or any amount therebetween. The treatment may be performed for a time period of about 1 to about 10 days, or any time interval therebetween, or for a time period of about 3 to about 7 days, or any time interval therebetween. For example, the treatment may be performed for a time period of 1, 2, 3, 4, 5, 6, 7, 8, 9 or 10 days, or any amount therebetween.

Following enzymatic hydrolysis, the aqueous phase containing the sugar, inorganic salts, and other soluble compounds may be separated from the insoluble, un-hydrolyzed solids phase to produce a soluble sugar stream (also referred to as the wash stream). The un-hydrolyzed solids are primarily lignin and cellulose, and, to a lesser extent, silica, insoluble salts and other compounds. The sugar stream can be pumped, mixed, and controlled more easily than a slurry containing liquids and insoluble solids. The insoluble solids are separated from the sugar stream by any suitable method, for example but not limited to plate and frame filtration, crossflow filtration, centrifugation, or other methods known to one of skill in the art.

Sugars present in the sugar stream, for example glucose, xylose, arabinose, mannose, galactose, or mixtures thereof, may be fermented by microbes. The fermentation products can include any desired products that generate value to the fermentation plant. The preferred fermentation products are ethanol and lactic acid, both of which have large markets and are made efficiently by many microbes. For ethanol production, fermentation can be carried out by one or more than one microbe that is able to ferment the sugars to ethanol. For example, the fermentation may be carried out by recombinant *Saccharomyces* yeast that has been engineered to ferment glucose, mannose, galactose and xylose to ethanol, or glucose, mannose, galactose, xylose, and arabinose to ethanol. Recombinant yeasts that can ferment xylose to ethanol are described in U.S. Pat. No. 5,789,210 (the contents of which are herein incorporated by reference). The yeast produces a fermentation broth comprising ethanol in an aqueous solution. For lactic acid production, the fermentation can be carried out by one or more than one microbe that ferments the sugars to lactic acid.

If ethanol is the product, the ethanol may then be recovered from the fermentation broth. For example, the ethanol may be recovered by distillation of the fermentation broth. After recovery of the ethanol, for example by distillation, further ethanol purification may be carried out by adsorption or other methods familiar to one of skill in the art. The aqueous stream after distillation is still and contains yeast cells, inorganic salts, unfermented sugars, organic salts and other impurities.

Inorganic salts present in the still bottoms may also be recovered using any suitable method known to one of skill in the art, for example, but not limited to ion exclusion. These processes can be followed by crystallization, electrodialysis, drying, or agglomeration and granulation. A preferred method for recovering the inorganic salt from the still bottoms is increasing the concentration of the still bottoms by evaporation, membrane filtration, or a combination thereof, followed by clarification by microfiltration, plate and frame filtration and centrifugation. This is followed by ion exclusion chromatography using a simulated moving bed (SMB) process and then crystallization, electrodialysis, drying, or agglomeration and granulation.

Inorganic salts may also be removed from the lignocellulosic feedstock prior to pretreatment by washing, leaching, or a combination thereof to produce a liquid stream or "leachate". An example of a leaching process is described in WO 02/070753 (Griffin et al., which is incorporated herein by reference). This process involves contacting the lignocellulosic feedstock with water for two minutes or longer, and then separating the solids from the aqueous phase. This decreases the acid requirement for pretreatment, and decreases costs, and degradation of xylose, in the pretreatment process.

After leaching, the aqueous solution containing salts (the "leachate") contains potassium and other salts and trace elements that may be of value for subsequent use, for example within a fertilizer. The leachate may be concentrated by evaporation or filtered through a reverse osmosis membrane to remove the water or subjected to reverse osmosis and evaporation. The leachate may be subsequently clarified by microfiltration, plate and frame filtration or centrifugation. Leachate salts can be separated from organics by ion exclusion chromatography using a simulated moving bed (SMB) process to produce a product that is useable as a fertilizer. Either the liquid or the solid salt streams obtained from the leachate can be combined with other salt streams produced as described herein.

With reference to FIG. 1, there is shown an outline of the method of the present invention for the processing of lignocellulosic feedstock (100) to sugar (300, 400) and ethanol (600), through the successive processes of pretreatment (200), enzymatic hydrolysis (300), sugar fermentation (400), and ethanol recovery (500). As indicated in this FIGURE, there are several steps leading to the production of ethanol where inorganic salt may be removed. For example, which is not to be considered limiting, inorganic salt may be removed at the stages indicated as 1, 2, 3, and 4 (150, 250, 350 and 550, respectively) in FIG. 1.

Following pretreatment with acid (200; FIG. 1), the lignocellulosic feedstock may be washed with water (250) to remove the inorganic salts at step 1. Prior to pretreatment, the acid, for example sulfuric acid, sulfurous acid, sulfur dioxide, or phosphoric acid, is added to the lignocellulosic feedstock to adjust the pH, for example, to about 0.4 to about 2.0, as described above. After pretreatment (200), the lignocellulosic feedstock is neutralized to a pH, for example, of about 4 to about 6 for example using ammonia or other alkali, as described above. The resulting inorganic salt can then be removed from the lignocellulosic feedstock at step 2 (250). The separation is carried out optionally by adding water to the pretreated lignocellulosic feedstock (200) and then separating the aqueous phase from the solids using a filter press, centrifuge or other suitable equipment. The aqueous stream (soluble stream) at this point is known as the pentose washings. The solids concentration in the pentose washings can be increased by evaporation, membrane filtration or a combination thereof.

The pentose washings containing ammonium sulfate and other inorganic salts can not be crystallized without further processing to remove the organic impurities. Ion exclusion by SMB chromatography can be used to separate the inorganic salts from the organic impurities. The inorganic salts can then be purified by crystallization or electrodialysis, drying, or agglomeration and granulation. The salt stream can then be used as a liquid fertilizer, or alternately dried and used as a solid fertilizer.

The resulting salt stream obtained following pretreatment of the lignocellulosic feedstock, either comprising sugars, or following removal of sugars, can be sold separately or combined with other salt streams obtained in the process described herein. For example, either the liquid or the solid salt streams obtained from the pentose washings can be combined with the salts from the leachate, indicated as step 1 in FIG. 1 (150), described above.

Preferably, the desalted sugar streams (pentose washings) are fermented to ethanol, since the desalted streams are easier to ferment than the streams containing salt.

The present invention also contemplates separating the aqueous salt and sugar stream from the un-hydrolyzed, insoluble solids following the enzymatic hydrolysis (300) at step 3 (350). The process for recovery of inorganic salts following enzymatic hydrolysis (300) at step 3 (350) is analogous to the process of salt recovery described above for pretreatment (200), at step 1 (150). For example, the wash stream obtained at step 3 (350) may be concentrated, or the sugars present in the wash stream obtained at step 3 removed and the remaining salt stream concentrated, and the sugar stream collected, or further processed at 400 (sugar fermentation) to produce ethanol.

The hydrolyzate stream produced following enzymatic hydrolysis (300), and containing salt and sugars is sent to fermentation (400), where yeast or other suitable microbes ferment the sugar to ethanol (600) or other products. If ethanol is made, it is recovered by distillation or other suitable means (500). The remaining slurry is the still bottoms (700) and contains unfermented sugars, inorganic salts, organic salts, yeast cells, and other compounds. The inorganic salts can be recovered from the still bottoms by means described above, and then used as desired, for example as a fertilizer.

Also shown in FIG. 1, is the removal of inorganic salts from the lignocellulosic feedstock prior to pretreatment (100) at step 1 (150). This may be carried out by leaching or other process, as described above.

The present invention may be illustrated in the following examples. However, it is to be understood that these examples are for illustrative purposes only, and should not be used to limit the scope of the present invention in any manner.

EXAMPLES

Example 1

Recovery of Soluble Inorganic Salt from a Hydrolyzate Sugar Stream

A sugar hydrolyzate stream containing sodium sulfate and other soluble inorganic salts was prepared as follows.

Feedstock Preparation

Wheat straw was received in bales measuring 3 feet by 3 feet by 4 feet. The wheat straw consisted of 60.3% carbohydrates, 18.7% lignin, 3.6% protein, 3.1% silica, and 4.9% non-silica inorganic salts. The inorganic salts included the cationic salt ions potassium (1.2%), calcium (0.57%), sodium (0.04%) and magnesium (0.15%), and the anionic ions chloride (0.22%) and phosphate (0.04%). The organic salt oxalate was also present at a concentration of 0.51%.

Two batches of 15 tonnes of the straw were hammer-milled to an average size of ⅛" and slurried in water at a ratio of 10 parts water to 1 part solids. The slurry was pumped through piping heated by direct injection with 350 psig steam to reach a temperature of 185° C. Once at this temperature, 10% sulfuric acid was added to reach a level of 0.9% acid on solids (w/w). The heated, acidified stock was held at this condition for 2 minutes as it passed through a pipe of 8 inches diameter. Upon exiting the pipe, the slurry was flashed through a series of three cyclones to drop the temperature to 70° C. and adjusted to pH 5.0 with 30% concentrated sodium hydroxide. The slurry was finally cooled to 50° C. by passing it through a heat exchanger cooled with cold water.

Upon acid addition, the soluble inorganic salts of potassium sulfate, sodium sulfate, and magnesium sulfate were formed. The insoluble salt, calcium sulfate, was also formed. Upon neutralization with sodium hydroxide, which is soluble, the concentration of sodium sulfate in the slurry increased markedly. The calcium sulfate concentration was above the solubility limit and a portion of it precipitated and deposited on the cyclones and related piping. A portion of the organic salt calcium oxalate also deposited on the equipment.

Hydrolysis

The neutralized, cooled pretreated slurry was then pumped into three hydrolysis tanks, each of working volume of about 130,000 liters. The tanks are equipped with bottom-mounted eductors to mix the slurry; one of the three tanks has two side-mounted agitators. The slurry consisted of 4.5% undissolved solids, and the undissolved solids consisted of 55% cellulose. Once the hydrolysis tanks were filled or the pretreated slurry was exhausted, cellulase enzyme from *Trichoderma reesei* was added. The enzyme dosage was 25 mg protein per gram cellulose, which corresponded to a cellulase activity of 25.4 Filter Paper Units (FPU) per gram of cellulose.

The hydrolyses ran for 5 days, at which point over 90% of the cellulose was converted to glucose. The final glucose concentration was 26.0 to 28.0 g/L, with an average of 27.5 g/L. The hydrolysis slurries were pumped to a Lasta plate and frame filter press to separate the un-hydrolyzed solid residue from the aqueous stream. A polymeric flocculent was added in line at a level of 1-3 kg polymer/t solids to improve the rate of filtration. The filter cake was 45% solids. The un-hydrolyzed solid residue contains primarily lignin and un-hydrolyzed cellulose, but also the insoluble salts such as calcium sulfate. The aqueous process stream is essentially free of insoluble particles and contains glucose, xylose, and arabinose sugar; the soluble salts sodium sulfate, potassium sulfate, magnesium sulfate, and a small amount of dissolved calcium sulfate; and acetic acid and other dissolved organics.

The process stream was evaporated under vacuum using a four-effect evaporator at 90° C., 80° C., 70° C. and 45° C., respectively, to a volume of 81,700 liters with a solids concentration of 34%. Some of the acetic acid evaporated with the water, and some solids precipitated upon evaporation. The pH of the evaporated slurry was adjusted to pH 6.5 with 50% sodium hydroxide solution, and this caused more precipitation. The concentrated, pH-adjusted stream was sent to the Lasta plate and frame filter press a second time, with a Perlite filter aid, to remove the precipitated solids. The clear, evaporated process stream had inorganic salt concentrations of 105 g/L sodium sulfate, 40 g/L potassium sulfate, and 5 g/L magnesium sulfate. In addition, organic compounds present included 153 g/L glucose, 49 g/L xylose, 7.3 g/L arabinose, 3.4 g/L furfural, 3.5 g/L hydroxymethyl furfural, and 9.1 g/L acetate salt, an organic salt that was measured as acetic acid, and various trace metals (including trace quantities of calcium), and a significant amount of unidentified impurities.

Ion Exclusion Chromatography

The inorganic, soluble salts sodium sulfate, potassium sulfate, and magnesium sulfate were recovered from the concentrated process stream by ion exclusion chromatography, as follows.

The ion exclusion chromatography separation was carried out over a 15-day period with continuous operation except for periodic shutdowns for filter changes and one complete cycle of water flushing. The separation was carried out on an Improved Simulated Moving Bed (ISMB) system (Eurodia Industrie S.A. of Wissous, France, available through Ameridia, Somerset, N.J.) of volume 6700 liters, packed with cation exchange resin from Mitsubishi Chemical, resin #UBK530. The ISMB system consists of 4 columns with 4 bed shifts per cycle and was operated with the feed stream at pH 5.8 to 6.5. The system was maintained at 70° C. as was the process feed and the dilution water. The process stream was fed at an average rate of 262 liters per hour and dilution water was added at a rate of 969 L/hr, which is an average ratio of 3.7:1 with the process feed. Salt raffinate and sugar product streams were collected at average flow rates of 760 and 461 liters/hr, respectively.

The salt raffinate stream contained over 99% of the salt. The inorganic salt concentrations were 35.6 g/L sodium sulfate, 14.4 g/L potassium sulfate, 1.9 g/L magnesium sulfate. In addition, the organic salt acetate was present at a concentration of 3.3 g/L, measured as acetic acid. A very small fraction of the organic compounds were present in this stream at concentrations of 1.2 g/L glucose, 0.5 g/L xylose, 0.2 g/L arabinose, 0.3 g/L furfural and 0.6 g/L hydroxymethyl furfural.

The sugar product stream contained the vast majority of the organic compounds and tiny amounts of salt. The concentrations of this stream were 1.2 g/L sodium sulfate, 0.4 g/L potassium sulfate, 66 g/L glucose, 22 g/L xylose, 3.3 g/L arabinose, and 0.09 g/L acetic acid, measured as acetate salt.

The salt raffinate stream is evaporated to 40% solids, then sent to an evaporator-crystallizer to produce granulates for use as fertilizer.

Example 2

Recovery of Soluble Inorganic Salt from Wheat Straw Leachate

Wheat straw was received in bales measuring 3 feet by 3 feet by 4 feet. The wheat straw consisted of 15.9% moisture. The composition of the straw, on a dry basis, was 60.1% carbohydrates, 19.7% lignin, 3.36% protein, 3.0% silica, and 4.5% non-silica salts. The inorganic cationic salt ions included 1.28% potassium, 0.45% calcium, 0.04% sodium, and 0.15% magnesium. The inorganic anions were chloride at 0.22% and 0.04% phosphate. The organic salt oxalate was present at a concentration of 0.55%. A weight of 1199 kg wet straw was hammer-milled to ⅛ inch.

The hammer-milled straw was slurried in 49,590 liters of 65° C. water. The slurry was gravity fed into a mixed tank, where it was mixed overnight for 18 hours and maintained at 65° C. The pH was 6.4 throughout the leaching process. The slurry was then flowed through screened baskets by gravity to separate the solids from the liquid leachate stream. The screened baskets produced a cake of 21.1% solids content.

The leachate contained 9.9% of the initial fiber solids. This was at a concentration of 2010 mg/L total dissolved solids, which included 127 mg/L protein, 262 mg/L potassium, 1.5 mg/L calcium, 36 mg/L magnesium, 55 mg/L chloride and a majority of 1530 mg/L unidentified. Other than calcium, which was not removed to a significant degree, the salts were removed from the straw by leaching at a yield of 87% to 93%. The protein yield in the leachate was 14%.

The leachate stream was evaporated to increase the solids concentration approximately 100-fold, to a solids concentration of 19.9% and a volume of 464 liters. A significant amount of protein precipitated and was removed by filtration. A preliminary evaluation of drying and crystallizing the filtrate indicated that the inorganic salts constituted much too small a proportion of the total solids for crystallization of the salts to be possible.

An aliquot of the leachate stream is fed to a laboratory ion exclusion chromatography system to separate the salts from the organics. The ion exclusion chromatography separation is carried out on a fixed bed of volume 127 mL, packed with cation exchange resin from Mitsubishi Chemical, resin #UBK530. The bed is operated with the feed stream at pH 6.8. The column is maintained at 70° C. as is the feed and the elution water. Prior to carrying out the separation, the column is conditioned with three bed volumes of the process stream. The process stream is fed in a pulse of 5 mL and elution water is then added at a rate of 4 mL/minute. Salt raffinate and sugar product streams are collected as the conductivity of the effluent indicates the presence and absence of salt, respectively.

The salt raffinate stream contains most of the inorganic salts, which are primarily potassium chloride and magnesium chloride and a small amount of organic impurities. The inorganic salt concentrations are high enough to permit crystallization to recover the salts.

Example 3

Recovery of Soluble Inorganic Salts from Wheat Straw Leachate

Wheat straw was received in bales measuring 3 feet by 3 feet by 4 feet. The wheat straw consisted of 6.4% moisture. The composition of the straw, on a dry basis, was 60.3% carbohydrates, 18.7% lignin, 3.6% protein, 3.1% silica, and 4.9% non-silica salts. The inorganic cationic salt ions present included 1.22% potassium, 0.57% calcium, 0.04% sodium, and 0.15% magnesium. The inorganic anions were chloride at 0.10%, 0.16% phosphate and 0.08% sulfate. A weight of 3,363 kg of moist straw was hammer-milled to ⅛ inch pieces. The hammer-milled straw was slurried in 70,626 liters of 65° C. water. The slurry was gravity fed into a mixed tank, where it was mixed overnight for 18 hours and maintained at 65° C. The pH was 4.9 throughout the leaching process. The slurry was then flowed through a centrifuge to separate the solids from the liquid leachate stream. The centrifuge produced a cake of 29.6% solids content.

The leachate contained 10.6% of the initial fiber solids. This was at a concentration of 4090 mg/L total dissolved solids, which included 1138 mg/L protein, 494 mg/L potassium, 67 mg/L calcium, 36 mg/L magnesium, 67 mg/L chloride, 80 mg/L of sulfate, 45 mg/L of phosphate, 27 mg/L of sodium, 163 mg/L of silica, 2010 mg/L of soluble phenolics and about 600 mg/L unidentified. Other than calcium and silica, which were not removed to a significant degree, the salts were removed from the straw by leaching at a yield of 50% to 93%. The protein yield in the leachate was 72%.

The leachate stream is evaporated to increase the solids concentration approximately 40-fold, to a solids concentration of 19.6% and a volume of 1770 liters. A significant amount of protein precipitates and is removed by filtration.

An aliquot of the leachate stream is fed to a laboratory ion exclusion chromatography system to separate the salts from the organics. The ion exclusion chromatography separation is carried out on a fixed bed of volume 127 mL, packed with cation exchange resin from Mitsubishi Chemical, resin #UBK530. The bed is operated with the feed stream at pH 6.8. The column is maintained at 70° C. as is the feed and the elution water. Prior to carrying out the separation, the column is conditioned with three bed volumes of the process stream. The process stream is fed in a pulse of 5 mL and elution water is then added at a rate of 4 mL/minute. Salt raffinate and sugar product streams are collected as the conductivity of the effluent indicates the presence of salt and water, respectively.

The salt raffinate stream contains most of the inorganic salts, which are primarily potassium chloride and magnesium chloride, and a small amount of organic impurities. The inorganic salt concentrations are high enough to permit crystallization to recover the salts.

Example 4

Recovery of Soluble Inorganic Salts During Conversion of Wheat Straw to Ethanol

A sugar hydrolyzate stream containing ammonium sulfate and other soluble inorganic salts was prepared as follows.

Wheat straw was received in bales measuring 3 feet by 3 feet by 4 feet and chopped and leached according to the procedures of Example 3. The leached wheat straw consisted of 57.1% carbohydrates, 36.6% lignin, 1.75% protein, 3.9% silica, and 0.8% non-silica salts. The salts included 0.2% potassium, 0.17% calcium, 0.05% sodium, 0.03% magnesium, <0.01% phosphate, 0.014% chloride and 0.023% sulfate. The leached straw was slurried in water at a ratio of 8 parts water to 1 part solids. The slurry was pumped through piping heated by direct injection with 350 psig steam to reach a temperature of 185° C. Once at this temperature, 10% concentrated sulfuric acid was added at a level of 0.9% acid on solids (w/w). The heated, acidified stock was held at this condition for 2 minutes as it passed through a pipe of 8 inches diameter. Upon exiting the pipe, the slurry was flashed through a series of three cyclones to drop the temperature to 75° C. and then cooled to 50° C. by using heat exchange with cool water. The slurry was then adjusted to pH 5.0 with concentrated ammonium hydroxide.

Upon acid addition, the soluble salts of potassium sulfate, sodium sulfate, and magnesium sulfate were formed. The insoluble salt, calcium sulfate, was also formed. Upon neutralization with ammonium hydroxide, which is soluble, the concentration of ammonium sulfate in the slurry increased markedly. The calcium sulfate concentration was above the solubility limit and a portion of it precipitated and deposited on the cyclones and related piping.

The neutralized, cooled pretreated slurry was then pumped into a hydrolysis tank at a volume of about 100,000 liters. The tank is equipped with side-mounted eductors to mix the slurry. The slurry consisted of 4.5% undissolved solids, and the undissolved solids consisted of 55% cellulose. Once the pretreated slurry was added to the hydrolysis tank, cellulase enzyme from *Trichoderma reesei* was added. The enzyme dosage was 35 mg protein per gram cellulose, which corresponded to a cellulase activity of 35.6 Filter Paper Units (FPU) per gram of cellulose.

The hydrolysis ran for 2 days, at which point over 90% of the cellulose was converted to glucose. The final glucose concentration was 26.0 to 28.0 g/L, with an average of 27.5 g/L. The hydrolysis slurry was pumped to a Lasta plate and frame filter press to separate the unhydrolyzed solid residue from the aqueous stream. A polyacrylamide flocculent was added at a level of 1-3 kg/t solids to aid in the filtration. The unhydrolyzed solid residue contains primarily lignin, unhydrolyzed cellulose and sand, but also the insoluble salts such as calcium sulfate. The aqueous process stream is essentially free of insoluble particles and contains glucose, xylose, and arabinose sugar; the soluble salts ammonium sulfate, potassium sulfate, magnesium sulfate and a small amount of dissolved calcium sulfate, and acetic acid, soluble lignin, and other dissolved organics.

The process stream was evaporated to increase the solids concentration three-fold by using a 4-effect falling film evaporator. The glucose concentration in the evaporated stream was 62 g/L, the xylose was 20 g/L, and the acetic acid was 2.0 g/L. The evaporated stream was filtered across the Lasta press with a Perlite filter aid to remove particulates.

The evaporated stream was pumped to a fermentor to carry out sugar fermentation with yeast. The yeast strain was LNHST from Purdue University and has been genetically modified to enable it to ferment xylose, as well as glucose, to ethanol. The strain was grown by propagation through successive fermentors, as described in U.S. Pat. No. 5,789,210. The fermentation was fed over a period of 7 hours and then run as a batch for 48 hours at a volume of 65,000 liters.

At the conclusion of the fermentation, the yeast cells were removed by centrifugation. The dilute beer was distilled to separate the ethanol from the aqueous solution. The distillation was carried out using a beer column and a rectifying column. The still bottoms were collected as a liquid stream from the bottom of the beer column with a volume of 87,000 liters.

The still bottoms were evaporated under vacuum at 80° C. to a volume of 18,000 liters with a solids concentration of 13%. Some of the solids precipitated upon evaporation. The pH of the evaporated slurry was adjusted to pH 7.0 with 30% ammonium hydroxide solution, and this caused more precipitation. The concentrated, pH-adjusted stream was sent to the Lasta press with a diatomaceous earth body feed to remove the precipitated solids. The clear, evaporated process stream had inorganic salt concentrations of 55 g/L ammonium sulfate, 20 g/L potassium sulfate, and 2.5 g/L magnesium sulfate. In addition, organic compounds present included 24 g/L xylose, 3.3 g/L arabinose, 3.4 g/L furfural, 3.5 g/L hydroxymethyl furfural, and 9.1 g/L acetate salt, an organic salt that was measured as acetic acid, and various trace metals (including trace quantities of calcium), and a significant amount of unidentified impurities.

The inorganic, soluble salts ammonium sulfate, potassium sulfate, and magnesium sulfate were recovered from the concentrated process stream by ion exclusion chromatography, as follows.

The ion exclusion chromatography separation is carried out over a 2.5-day period with continuous operation except for periodic shutdowns for filter changes and one complete cycle of water flushing. The separation is carried out on an Improved Simulated Moving Bed (ISMB) system (Eurodia Industrie S.A. of Wissous, France, available through Ameridia, Somerset, N.J.) of volume 6700 liters, packed with cation exchange resin from Mitsubishi Chemical, resin #UBK530. The ISMB system consists of 4 columns with 4 bed shifts per cycle and is operated with the feed stream at pH 6.0 to 7.5. The system is maintained at 65° C. as was the process feed and the dilution water. The process stream is fed at an average rate of 320 liters per hour and dilution water was added at a rate of 960 L/hr, which is an average ratio of 3.0:1 with the process feed. Salt raffinate and sugar product streams are each collected at average flow rates of 640 liters/hr.

The salt raffinate stream contains over 99% of the salt. The inorganic salt concentrations are 15.6 g/L ammonium sulfate, 4.4 g/L potassium sulfate, and 1.9 g/L magnesium sulfate. In addition, the organic salt acetate is present at a concentration of 0.9 g/L, measured as acetic acid. A very small fraction of the organic compounds were in this stream at concentrations of 0.5 g/L xylose, 0.2 g/L arabinose, 0.3 g/L furfural, and 0.6 g/L hydroxymethyl furfural.

The sugar product stream contained the vast majority of the organic compounds and very small amounts of salt. The concentrations of this stream were 1.2 g/L ammonium sulfate, 0.4 g/L potassium sulfate, 14 g/L xylose, 2.3 g/L arabinose, and 0.09 g/L acetic acid, measured as acetate salt.

The salt raffinate stream is evaporated to 40% solids, then sent to an evaporator-crystallizer to produce granulates for use as fertilizer.

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

Thompson, D., Shaw, P. G. and Lacey, J. A. (2003) Post-Harvest Processing Methods for Reduction of Silica and Alkali Metals in Wheat Straw In Applied Biochemistry and Biotechnology 105-108:205-218.

Wooley, R., Ruth, M., Sheehan, J., Ibsen, K., Majdeski, H. and Galvez, A. (1999) Lignocellulosic Biomass to Ethanol Process Design and Economics Utilizing Co-Current Dilute Acid Prehydrolysis and Enzyme Hydrolysis Current and Future Scenarios, Technical Report, National Renewable Energy Laboratory pp. 16-17.

What is claimed is:

1. A process, comprising the steps of:
a) washing or leaching a lignocellulosic feedstock comprising inorganic salts which comprise at least potassium and calcium ions with an aqueous solution for a sufficient time to produce an aqueous leachate stream, wherein the washing or leaching duration and the pH of the aqueous solution are sufficient to extract inorganic ions comprising potassium from the feedstock while substantially retaining calcium ions in the feedstock to produce i) an aqueous leachate stream comprising inorganic salts that are substantially free of calcium and ii) a solid leached or washed feedstock;
b) removing the aqueous leachate stream from the leached or washed feedstock;
c) pretreating the leached or washed feedstock with acid to produce a pretreated lignocellulosic feedstock comprising at least pentose sugar;
d) fermenting the pentose sugar with at least one microbe;
e) concentrating said aqueous leachate stream produced in step (a) by evaporation, filtering through a reverse osmosis membrane, or a combination thereof; and f) recovering a concentrated aqueous leachate stream produced in step (e).

2. The method of claim 1, wherein the lignocellulosic feedstock is selected from the group consisting of corn stover, wheat straw, barley straw, canola straw, rice straw, oat straw, soybean stover, grass, switch grass, miscanthus, cord grass, and reed canary grass, aspen wood, sawdust, bagasse, beet pulp and mixtures thereof.

3. The method of claim 1, wherein the lignocellulosic feedstock contains from about 0.2% to about 4% (w/w) potassium.

4. The method of claim 1, wherein the inorganic salts of the aqueous leachate stream are recovered by ion exclusion in the recovering step.

5. The method of claim 4, further comprising crystallization electrodialysis, drying, or agglomeration and granulation of the inorganic salts.

6. The method of claim 1, wherein the pretreatment comprises a method selected from the group consisting of batch dilute acid hydrolysis, continuous dilute acid hydrolysis, steam explosion and extrusion.

7. The method of claim 1, wherein the acid in the pretreatment is selected from the group consisting of sulfuric acid, sulfurous acid, sulfur dioxide, phosphoric acid, and a combination thereof.

8. The method of claim 7, wherein the acid is sulfuric acid.

9. The method of claim 1, wherein the pretreating is performed at a temperature from about 160° C. to about 280° C., at a pH from about pH 0.4 to about 2.0 and for a period of from about 0.1 to about 30 minutes.

10. The method of claim 1, wherein the fermenting produces a fermentation broth comprising ethanol and wherein the fermentation broth is distilled to produce concentrated ethanol and still bottoms.

11. The method of claim 10, further comprising recovering the inorganic salt from the still bottoms followed by purifying the inorganic salt.

12. The method of claim 11, wherein prior to the step of recovering the inorganic salt from the still bottoms, the concentration of the still bottoms is increased by evaporation, or membrane filtration, to produce concentrated still bottoms, followed by a step of ion exclusion chromatography using a simulated moving bed process.

13. The method of claim 12, wherein prior to the step of ion exclusion chromatography, the concentrated still bottoms are clarified by microfiltration, plate and frame filtration or centrifugation.

14. The method of claim 13, wherein the step of purifying the inorganic salt comprises crystallization, electrodialysis, drying, or agglomeration and granulation.

15. The method of claim 1, wherein the concentrated aqueous leachate stream is combined with a soluble inorganic salt stream obtained from the pretreated feedstock, the neutralized feedstock, or the sugar stream to produce a combined salt stream.

16. The method of claim 15, wherein the salt present in the combined salt stream is concentrated by evaporation, or membrane filtration to produce a concentrated salt solution.

17. The method of claim 16, wherein the concentrated salt solution is clarified to produce a clarified salt solution.

18. The method of claim 17, wherein the inorganic salt is recovered from the clarified salt solution by ion exclusion chromatography.

19. The method of claim 1, wherein in the pretreatment, at least a portion of hemicellulose in the feedstock is hydrolyzed to produce one or more than one sugar monomer selected from the group consisting of xylose, arabinose, mannose, galactose and a combination thereof.

20. The method of claim 1, wherein the inorganic salt is soluble.

21. The process of claim 1, further comprising combining the concentrated aqueous leachate stream with a process stream comprising salt generated in said process.

22. A process for recovering inorganic salt, comprising the steps of:
   a) washing or leaching a lignocellulosic feedstock comprising inorganic salts which comprise at least potassium and calcium ions with an aqueous solution for a sufficient time to produce an aqueous leachate stream, wherein the washing or leaching duration and the pH of the aqueous solution are sufficient to extract inorganic ions comprising potassium from the feedstock while substantially retaining calcium ions in the feedstock to produce i) an aqueous leachate stream comprising inorganic salts that are substantially free of calcium and ii) a solid leached or washed feedstock;
   b) removing the aqueous leachate stream from the leached or washed feedstock;
   c) pretreating the washed or leached lignocellulosic feedstock with acid to produce a pretreated lignocellulosic feedstock;
   d) adding soluble base to the pretreated lignocellulosic feedstock to produce a neutralized feedstock having a pH of about 4.0 to about 6.0;
   e) enzymatically hydrolysing the neutralized feedstock to produce a sugar stream and an enzyme hydrolyzed feedstock;
   f) fermenting the sugar stream to produce a fermentation broth comprising ethanol;
   g) distilling the fermentation broth to produce concentrated ethanol and still bottoms;
   h) further purifying the ethanol produced in step (g);
   i) concentrating said aqueous leachate stream produced in step (b) by evaporation, filtering through a reverse osmosis membrane, or a combination thereof; and
   j) recovering a concentrated aqueous leachate stream produced in step (i).

23. The method of claim 22, wherein the pretreating is performed at a temperature from about 160° C. to about 280° C., at a pH from about pH 0.4 to about 2.0 and for a period of from about 0.1 to about 30 minutes.

24. The method of claim 22, further comprising separating the sugar stream from the enzyme hydrolyzed feedstock to form a solid residue and a sugar hydrolyzate stream.

25. The method of claim 24, wherein the inorganic salt is concentrated by evaporation or membrane filtration.

26. The method of claim 22, wherein in the enzymatic hydrolysis, cellulase enzyme is added to the neutralized feedstock to hydrolyze at least a portion of cellulose in the neutralized feedstock and produce glucose.

27. The process of claim 22, further comprising combining the concentrated aqueous leachate stream with a process stream comprising salt generated in said process.

* * * * *